United States Patent [19]

Notsu et al.

[11] Patent Number: 5,635,046

[45] Date of Patent: Jun. 3, 1997

[54] METHOD FOR DRYING POLYACRYLAMIDE GEL AFTER ELECTROPHORESIS

[75] Inventors: Kazuaki Notsu; Mieko Shiratori, both of Ryugasaki, Japan

[73] Assignee: Daiichi Pure Chemicals Co., Ltd., Tokyo, Japan

[21] Appl. No.: 694,459

[22] Filed: Aug. 7, 1996

[30] Foreign Application Priority Data

Aug. 16, 1995  [JP]  Japan ................................. 7-208644

[51] Int. Cl.⁶ ........................ G01N 27/26; G01N 27/447
[52] U.S. Cl. ........................ 204/462; 204/613; 34/305
[58] Field of Search ............................ 204/462, 613, 204/456, 457, 458, 459, 461, 463, 464, 465, 466, 467, 468, 469, 470, 606, 607, 608, 609, 610, 612, 614, 615, 616, 617, 618, 619, 620, 621; 34/237, 305, 303, 238, 239

[56] References Cited

U.S. PATENT DOCUMENTS 3,523,863  8/1970  Juhos ................................ 204/462 X
5,440,822  8/1995  Alpenfels et al. ........................ 34/305

OTHER PUBLICATIONS

J.W. Mayer, "Simple and Rapid Methods for Drying Polyacrylamide Gels After Isoelectric Focusing" Analytical Biochemistry 76 (1976) 369–373.

Douglas Prasher and Bonnie Woodward, "Fixation and Drying of DNA Sequencing Gels on Glass Plates" BioTechniques vol. 8 No. 4 (1990) 391–393.

Yi–Lin Yan "A Simple and Inexpensive Method for Drying High–Percentage Polyacrylamide Gradient Gels" BioTechniques vol. 8 No. 4 (1990) 381–382.

David R. Porter and Mark J. Gatschet, "Simplified Drying of Polyacryiamide Gels for Fluorography" BioTechniques vol. 13 No. 3 (1992) 364–365.

Babru Bahan Samal, "Drying and Storage of Polyacrylamide Slab Gels: A Simple Procedure" Analytical Biochemistry 163 (1987) 42–44.

Ľudevit Škultéty and Rudolf Tomar, "Improved procedure for the drying and storage of polyacrylamide slab gels" Journal of Chromatography, 582 (1992) 249–252.

M. Krishnan and Henry T. Nguyen, "Drying Acrylamide Slab Gels for Fluorography Without Using Gel Drier and Vacuum Pump" Analytical Biochemistry, 187 (1990) 51–93.

Reiner Westermann, "Simple Drying of Polyacrylamide Gels for Fluorography and Storage" Electrophoresis, 6 (1985) 136–137.

Octavian Popescu, "A Simple Method for Drying Polyacrylamide Slab Gels Using Glycerol and Gelatin" Electrophoresis, 4 (1983) 432–433.

*Primary Examiner*—Kathryn L. Gorgos
*Assistant Examiner*—John S. Starsiak, Jr.
*Attorney, Agent, or Firm*—Oblon, Spivak, McClelland, Maier & Neustadt, P.C.

[57] ABSTRACT

A polyacrylamide gel which has undergone electrophoresis is dried in the presence of pressure applied via a semipermeable film placed on the gel. Before applying the semipermeable film onto the gel, solution components contained in the gel is replaced by an aqueous solution containing one or more substances selected from the group consisting of saccharides, sugar alcohols having 4 or more carbon atoms, and water-soluble polymers. According to this method, a polyacrylamide gel which has undergone electrophoresis can be dried with ease and reduced costs while maintaining its transparency and without causing cracks even in the case of a gel containing polyacrylamide gel at a high concentration.

7 Claims, No Drawings

METHOD FOR DRYING POLYACRYLAMIDE GEL AFTER ELECTROPHORESIS

BACKGROUND OF THE INVENTION

1. Field of the Invention

The present invention relates to a simple and economical method for drying a polyacrylamide gel which has undergone electrophoresis, while maintaining its transparency and without causing cracks.

2. Background Art

Polyacrylamide gels are very often used in electrophoresis analyses of biological macromolecules such as proteins and nucleic acid.

A polyacrylamide gel which has been used for performing electrophoresis of a biological sample and has been stained with a dye or the like cannot be stored for a prolonged period as it becomes brittle if left as is. Therefore, in many cases, profiles of electrophoresis are photographed or copied on paper or the like and stored as images.

However, photographing and copying involve difficulty in recording accurately thin bands or very subtle differences in density of stains. In addition, biological macromolecules which have been separated by electrophoresis cannot be recovered.

Therefore, it has been attempted to dry, for storage, a gel which has undergone electrophoresis, and a variety of methods have been proposed. For example, Japanese Patent Application Laid-open (kokai) No. 61-79151 discloses a method in which a heating plate provided exclusively for the purpose of drying is used and the gel is brought to dryness while being pressed against a support such as filter paper under reduced pressure. Japanese Patent Application Laid-open (kokai) No. 1-147356 discloses a method in which a gel is plasticized after being dewatered using an organic solvent. According to another method, a gel is sandwiched between semipermeable transparent films such as cellophane film before drying.

However, a method in which gels are dried with heat under reduced pressure requires a dedicated drying apparatus and a vacuum pump, which are both relationely expensive. In addition, when gels contain acrylamides at high concentrations of not less than 15% by weight, it often happens that gels are damaged due to cracking. In a method in which gels are dewatered using an organic solvent, gels tend to lose transparency or to deform, raising a problem in recording images accurately.

Compared to the above methods, a method in which gels are dried after being sandwiched between cellophane films or the like (hereinafter referred to as a cellophane sandwich method) is advantageous because it does not require special apparatuses. Moreover, it suppresses deformation of a gel during the drying process. Briefly, in this cellophane sandwich method, a gel is sandwiched between two films such as cellophane films or between a film such as cellophane and a plastic sheet, and the gel is dried while being pressed, making use of accompanying shrinking force of the films in the course of drying.

However, previous cellophane sandwich methods have a drawback similar to that involved in the above mentioned method involving heating under reduced pressure. That is, especially when using gels containing polyacrylamides at high concentrations of not less than 15% by weight, gels tend to generate cracks, thus impairing accurate recording of invaluable results of electrophoresis.

To avoid this problem, a number of methods have been proposed including incorporation of glycerol in a gel and application of gelatin or a paste onto the surface of a gel. However, any methods have turned out to be still uneffective for preventing the occurrence of cracks in the case of using gels having high concentrations of acrylamide.

Under the above circumstances, the present inventors conducted extensive studies and found that a polyacrylamide gel containing an acrylamide at a high concentration can be dried in a good state without causing cracks, if a polyacrylamide gel which has undergone electrophoresis is immersed in a solution containing one or more substances selected from the group consisting of saccharides, sugar alcohols having 4 or more carbon atoms, and water-soluble polymers; thereby impregnating the gel therewith before the gel is sandwiched between semipermeable transparent films such as cellophane. The present invention was accomplished based on this finding.

SUMMARY OF THE INVENTION

Accordingly, the present invention provides a method, for drying, while applying a pressure using a semipermeable film, a polyacrylamide gel which has been used for electrophoresis, wherein solution components contained in the gel are replaced by an aqueous solution containing one or more substances selected from the group consisting of saccharides, sugar alcohols having 4 or more carbon atoms, and water-soluble polymers, after which the gel is pressed using a semipermeable film for drying.

The above and other objects, features, and advantages of the present invention will become apparent from the following description.

DETAILED DESCRIPTION OF PREFERRED EMBODIMENTS

The polyacrylamide gel to be dried according to the method of the present invention is not particularly limited so far as it can be used for electrophoresis. For example, it may be a polyacrylamide gel having an arbitrary concentration or density gradient of gel ranging from 2 to 50% by weight. The gel is used in electrophoresis of samples to be analyzed in accordance with known methods described in a manual for electrophoresis, for example, in "Electrophoresis— Fundamentals and Experiments" (edited by Hiroshi Terada). Alternatively, an acrylamide monomer solution having a high concentration, a peroxide solution having a low concentration, and a solution of a reducing agent having a low concentration are mixed at an arbitrary ratio, after which the resultant mixture is introduced into a support for gel (Japanese Patent Application Laid-open (kokai) No. 5-203621) to obtain a polyacrylamide gel, which is used either in a known method of gel electrophoresis or in a method in which a buffer used for performing electrophoresis is selected from the group consisting of Tris-tricin buffers, Tris-bicin buffers, Tris-2-(N-morpholino) ethanesulfonic acid buffers, and Tris-N-(acetamide)-2-aminoethanesulfonic acid buffers (Japanese Patent Application Laid-open (kokai) No. 6-34602).

Saccharides which are used in the present invention include monosaccharides such as glucose and mannose, as well as disaccharides such as sucrose and lactose. Of these, disaccharides are preferred with sucrose being particularly preferred. These saccharides may be used singly or in combination of two or more.

Examples of water-soluble polymers used in the present invention include polyethylene glycol, polyvinyl alcohol, polyvinylpyrrolidone, and polypropylene glycol. Of these, water-soluble polymers each having a molecular weight of 200–5000, particularly polyethylene glycol and polypropylene glycol each having a molecular weight of 200–5000, are preferred. These water-soluble polymers may be used singly or in combination of two or more.

The molecular weight of a water-soluble polymer is not particularly limited. However, considering that a solution component such as an aqueous solution contained in a polyacrylamide gel is to be replaced by a solution of the water-soluble polymer, the molecular size of a water-soluble polymer is preferably smaller than the unit size of the network structure of a polyacrylamide gel. Specifically, it is preferred to use a water-soluble polymer having a molecular weight of not more than 5,000. It is possible to use two or more polymers having different molecular weights from one another.

In aqueous solutions to be used in the present invention, the concentration of one or more members selected from the group consisting of saccharides, sugar alcohols, and water-soluble polymers is preferably from 0.01 to 98% by weight. In order to maintain transparency of a gel and to dry it quickly, the concentration of 0.1–20% by weight is particularly preferred.

The above-described aqueous solution which is used in the present invention may contain, if needed, water-soluble and highly volatile organic solvents. Examples of such organic solvents include C1–C4 alcohols such as methanol, ethanol, 1-propanol, 2-propanol, and butanol, as well as acetone. In the present invention, methanol, ethanol, 1-propanol, and 2-propanol are preferred. The organic solvents may be used singly or in combination of two or more. It is preferred that the organic solvents be present in amounts of 0.1–80% by weight, and more preferably 1–50% by weight, in the aforementioned aqueous solution.

In order to replace a solution component contained in a polyacrylamide gel which has been used for electrophoresis by the above-described aqueous solution, the polyacrylamide gel to dry is immersed in the aqueous solution for at least 1 minute and preferably for 20 minutes to 24 hours. When the aqueous solution is stirred or shaken, the time required for replacement of the components in a polyacrylamide gel can be reduced. The volume of the aqueous solution is preferably at least equivalent to that of the polyacrylamide gel to dry, and particularly preferably at least 4 times that of the gel. The polyacrylamide gel used for electrophoresis is preferably washed with water or the like before being immersed in the aqueous solution.

A polyacrylamide gel in which the solution components in the gel have been replaced by the aforementioned aqueous solution is dried while applying, under pressure, a semipermeable film onto either surface or both surfaces of the gel. The gel may be dried while being left at room temperature. In the case of applying a semipermeable film onto one surface of a gel, the gel may be sandwiched between the semipermeable film and another film such as a plastic film. As the semipermeable film, transparent film made of cellophane may be used.

According to the present invention, a polyacrylamide gel which has undergone electrophoresis can be dried with ease and reduced costs while maintaining its transparency and without causing cracks even when the gel contains polyacrylamide at a high concentration.

EXAMPLES

The present invention will next be described by way of examples, which should not be construed as limiting the invention.

Example 1

A polyacrylamide gel which was used under the following conditions for SDS-polyacrylamide gel electrophoresis (SDS-PAGE) was dried.

(1) Polyacrylamide gel:
0.35M Tris-HCl buffer
15–25% gradient gel
Gel size: 84 mm×90 mm×1.0 mm (2) Sample used for electrophoresis:
a. Protein molecular weight marker III "Daiichi"
(product of Daiichi Pure Chemicals)
A sample was prepared in accordance with the manufacturer's instructions provided in the users' manual, and was applied onto each well in the gel in an amount of 5 µl.
b. Peptide molecular weight marker "Daiichi"
(product of Daiichi Pure Chemicals)
A sample was prepared in accordance with the manufacturer's instructions provided in the users' manual, and was applied onto each well in the gel in an amount of 5 µl.

(3) Buffer for electrophoresis:
0.025M Tris—0.192M glycine+0.1% SDS (4) Current:
40 mA Constant current, approximately 1 hour.

(5) Staining and discoloration:
A gel used which had been for electrophoresis was shaken in a CBB staining liquid (0.04% Coomassie Brilliant Blue+30% methanol+10% acetic acid) for about 2 hours, after which the gel was transferred into a liquid for discoloration (5% methanol+7.5% acetic acid). The liquid for discoloration was changed as needed until proper staining results were obtained.

(6) Drying of a gel:
After washing the discolored gel using purified water, the gel was shaken in 50 ml of a 40% aqueous methanol solution containing 5% sucrose for about 1 hour. Subsequently, the gel was sandwiched between 2 transparent cellophane sheets which had been swollen in water. The sandwiched gel was dried by being stuck onto a glass plate using a clip and left for a whole day and a night in the laboratory room. As a result, the resultant dry polyacrylamide gel maintained its transparency and did not have any cracks. After the dry gel was stored in a container together with a dessicant, no change was observed for 2 years.

Example 2

The general procedure of Example 1 was repeated excepting that the solution for soaking a polyacrylamide gel described under item (6) in Example 1 was changed to a 40% aqueous methanol solution containing 5% mannitol. As a result, the resultant dry polyacrylamide gel maintained its transparency and did not have any cracks.

Example 3

The general procedure of Example 1 was repeated excepting that the solution for soaking a polyacrylamide gel described under item (6) in Example 1 was changed to a 40% aqueous methanol solution containing 7.5% polyethylene glycol 200 (product of Kishida Kagaku).

As a result, the resultant dry polyacrylamide gel maintained its transparency and did not have any cracks. After the dry gel was stored in a container together with a dessicant, no change was observed for 2 years.

Comparative Example

The general procedure of Example 1 was repeated excepting that the solution for soaking a polyacrylamide gel described under item (6) in Example 1 was changed to a 40% aqueous methanol solution. As a result, the resultant dry polyacrylamide gel was cracked at the site close to its center and broken into two pieces.

What is claimed is:

1. A method for drying, while applying a pressure using a semipermeable film, a polyacrylamide gel which has been used for electrophoresis, comprising the steps of:

replacing solution components contained in the gel by an aqueous solution containing one or more substances selected from the group consisting of saccharides, sugar alcohols having 4 or more carbon atoms, and water-soluble polymers, and subsequently, applying a semipermeable film onto the polyacrylamide gel with pressure, thereby drying the gel.

2. The method according to claim 1, wherein the saccharides are monosaccharides and disaccharides.

3. The method according to claim 1, wherein the sugar alcohols have 4–6 carbon atoms.

4. The method according to claim 1, wherein the water-soluble polymers are polyethylene glycol, polypropylene glycol, polyvinyl alcohol, and polyvinylpyrrolidone.

5. The method according to claim 1, wherein the concentration, in the aqueous solution, of the one or more substances selected from the group consisting of saccharides, sugar alcohols having 4 or more carbon atoms, and water-soluble polymers is 0.1–20% by weight.

6. The method according to claim 1, wherein the aqueous solution further contains 0.1–80% by weight of C1–C4 alcohol or acetone.

7. The method according to claim 1, wherein the replacement of the solution components is performed by immersing the polyacrylamide gel in the aqueous solution for 10 minutes to 24 hours.

* * * * *